United States Patent [19]

Mizuno et al.

[11] Patent Number: 4,820,316
[45] Date of Patent: Apr. 11, 1989

[54] METHOD OF FORESEEING BREAK-THROUGH IN GAS ADSORBING APPARATUS

[75] Inventors: Hisayuki Mizuno; Masao Miura; Hiroyuki Fukushima, all of Ube; Mamoru Miyamoto, Ichihara; Kyouhei Ohizumi, Ichihara; Yoshio Nishimura, Ichihara, all of Japan

[73] Assignee: Ube Industries, Ltd., Ube, Japan

[21] Appl. No.: 82,932

[22] Filed: Aug. 5, 1987

Related U.S. Application Data

[63] Continuation of Ser. No. 774,294, Sep. 10, 1985, abandoned.

[30] Foreign Application Priority Data

| Sep. 11, 1984 | [JP] | Japan | 59-191267 |
| Feb. 22, 1985 | [JP] | Japan | 60-35065 |
| Jun. 28, 1985 | [JP] | Japan | 60-140209 |
| Jul. 26, 1985 | [JP] | Japan | 60-165242 |

[51] Int. Cl.⁴ ............................................. B01D 53/04
[52] U.S. Cl. ......................................... 55/18; 55/71; 55/74
[58] Field of Search ............... 55/18, 71, 160–163, 55/270, 274, 275, 387, 31, 33, 35; 436/124, 126, 182; 73/29, 73

[56] References Cited

U.S. PATENT DOCUMENTS

| 2,278,854 | 4/1942  | Hunsicker       | 55/161    |
| 2,297,763 | 10/1942 | Higley et al.   | 55/161    |
| 2,328,521 | 8/1943  | Wittmann        | 55/163    |
| 2,411,039 | 11/1946 | Heuser          | 55/161 X  |
| 2,506,578 | 5/1950  | Case            | 55/161    |
| 2,511,666 | 6/1950  | Barr            | 55/161    |
| 2,572,009 | 10/1951 | Carson          | 55/161    |
| 2,575,169 | 11/1951 | Green, Jr.      | 73/73     |
| 2,692,497 | 10/1954 | Van Nordstrand  | 73/73 X   |
| 2,951,156 | 8/1960  | Miller          | 55/18 X   |
| 3,037,337 | 6/1962  | Gardner         | 55/71 X   |
| 3,116,132 | 12/1963 | Haller et al.   | 55/71 X   |
| 3,388,993 | 6/1968  | Peterson et al. | 55/71 X   |
| 3,715,866 | 2/1973  | Chatlos et al.  | 55/270 X  |
| 4,154,586 | 5/1979  | Jones et al.    | 55/274    |

FOREIGN PATENT DOCUMENTS

| 636162 | 4/1928 | France | 55/161 |
| 68536  | 4/1986 | Japan  | 55/18  |

OTHER PUBLICATIONS

Ellis et al., Analytical Chemistry, vol. 21, No. 11, Nov. 1949, pp. 1345–1348, "Colorimetric Determination of Boron Using 1,1'-Dianthrimide".

Snell, "Photometric and Fluorometric Methods of Analysis of Nonmetals", 1981, pp. 170, 171, 198–200.

*Primary Examiner*—Robert Spitzer
*Attorney, Agent, or Firm*—Frishauf, Holtz, Goodman & Woodward

[57] ABSTRACT

In a method of foreseeing or detecting break-through of a gas in a gas-adsorbing apparatus utilizing a gas-adsorbing material, the improvement in which the break-through is foreseen or detected by detecting a weight of the gas adsorbed by the gas-adsorbing material. When the gas to be detected contains boron trichloride, the break-through can be foreseen or detected by detecting a color change of a detecting agent such as 1,1'-dianthrimide or a combination of caraminic acid, hydrochloric acid and sulfuric acid, the detecting agent being arranged in a lower stream following the gas-adsorbing material and which shows a color change upon contact with boron trichloride.

6 Claims, 1 Drawing Sheet

METHOD OF FORESEEING BREAK-THROUGH IN GAS ADSORBING APPARATUS

This application is a continuation of application Ser. No. 774,204, filed Sept. 10, 1985 now abandoned.

FIELD OF THE INVENTION

This invention relates to a method of foreseeing or detecting break-through in a gas-adsorbing apparatus. Particularly, this invention relates to a method of foreseeing or detecting break-through of a gas containing boron trichloride in a gas-adsorbing apparatus.

DESCRIPTION OF PRIOR ARTS

A variety of toxic liquids or gases such as chlorinated hydrocarbons, e.g., carbon tetrachloride and trichlorethylene, boron trichloride, halogen gases, ammonia gas, and silane gas ($SiH_4$) are employed in industry as reactive materials, solvents, washing solvents, dispersing media, etc. Particularly, a chlorine-containing compound such as carbon tetrachloride or boron trichloride is generally employed in a process of production of LSI (i.e., large scale integrated) circuits for dry-etching of an aluminum substrate or others by continuously bringing a chlorine-containing compound in a gaseous state into contact with the aluminum substrate or others. A large volume of silane gas is generally employed in a process of production of LSI circuits utilizing a plasma CVD.

The toxic compounds such as above likely cause air pollution if these are released without treatment. Accordingly, release of waste gases containing these toxic compounds into atmospheric air is under strict control.

Therefore, in most cases, these toxic compounds are removed from a waste gas in an apparatus capable of removing these toxic compounds which is arranged in a lower stream following the device using these compounds. The waste gas is then released into air. For instance, carbon tetrachloride or boron trichloride is employed for the dry-etching and then the waste gas is processed in a gas-adsorbing apparatus containing a gas-adsorbing material such as activated charcoal to remove the toxic compound from the waste gas. Other toxic compounds such as silane gas employed in a process of producing LSI using plasma CVD can be removed in a similar apparatus.

The gas-adsorbing apparatus using a gas-adsorbing material undergoes break-through when the material adsorbs a certain amount corresponding to the gas-adsorbing capacity of the material. After the break-through occurs, the gas-adsorbing material is not able to effectively adsorb the gas. Accordingly, the toxic gas introduced into the gas-adsorbing apparatus after the break-through takes place passes freely through the apparatus to be released into air. For this reason, the gas-adsorbing apparatus or the gas-adsorbing material which adsorbs the gas up to the full capacity should be replaced with a new one. In other words, the gas-adsorbing apparatus or the gas-adsorbing material contained in the apparatus should be replaced in advance before the break-through starts or immediately after the break-through starts.

In the prior art, the break-through is detected by observing a color change of a material such as a pH indicator which is arranged in a lower stream following the gas-adsorbing material and which shows a color change upon contact with an acidic material such as boron trichloride. However, the pH indicator is not sufficiently sensitive to detect a small amount of a released gas.

SUMMARY OF THE INVENTION

An object of this invention is to provide a method of foreseeing or detecting the break-through of a gas in a gas-adsorbing apparatus.

Another object of the invention is to provide a method of foreseeing the break-through of a gas in a gas-adsorbing apparatus.

A further object of the invention is to provide a method of foreseeing or detecting the break-through of a gas containing boron trichloride in a gas-adsorbing apparatus.

A still further object of the invention is to provide a method of detecting with high sensitivity break-through of a gas containing boron trichloride in a gas-adsorbing apparatus.

In a primary aspect, the present invention resides in a method of foreseeing or detecting break-through of a gas in a gas-adsorbing apparatus utilizing a gas-adsorbing material, which is improved in that the break-through is foreseen or detected by detecting the weight of the gas adsorbed by the gas-adsorbing material.

In a secondary aspect, the invention resides in a method of foreseeing or detecting break-through of a gas containing boron trichloride in a gas-adsorbing apparatus utilizing a gas-adsorbing material, which is improved in that the break-through is foreseen or detected by detecting a color change of a detecting agent selected from the group consisting of 1,1'-dianthrimide and a combination of carminic acid, hydrochloric acid and sulfuric acid, the detecting agent being arranged in a lower stream following the gas-adsorbing material and which shows a color change upon contact with boron trichloride.

The foreseeing or detecting of the break-through can be aided with an alarm signal such as the sound of a buzzer or flicker of a lamp.

DETAILED DESCRIPTION OF THE INVENTION

Figure 1:
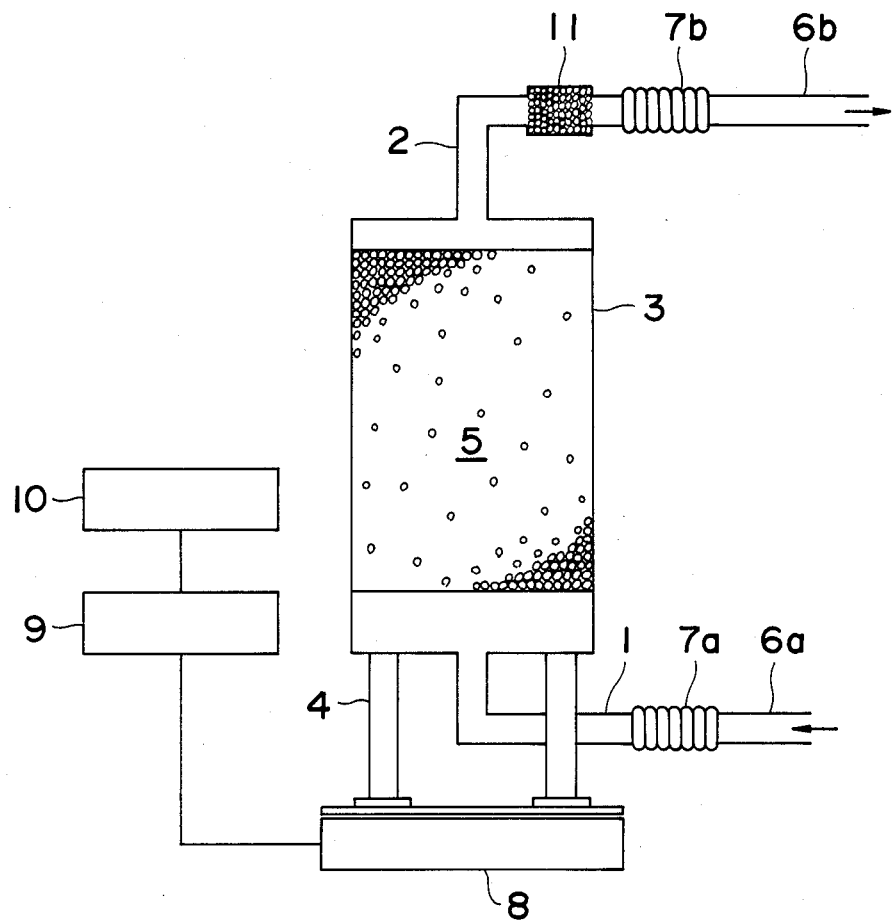
FIG. 1 schematically shows a representative gas-adsorbing apparatus to which a system according to the present invention is applied.

The present invention is further described with reference to the attached drawing.

The system illustrated in FIG. 1 comprises a gas-adsorbing apparatus in combination of a means of foreseeing or detecting break-through of a gas to be adsorbed in the gas-adsorbing apparatus, as well as pipe line systems.

There is no specific limitation on the gas-adsorbing apparatus with respect to the shape, volume, etc., as far as it contains an appropriate gas-adsorbing material.

As an embodiment of the adsorbing apparatus, there can be mentioned a tower or cylinder type gas-adsorbing apparatus as seen in FIG. 1 which is composed of a tower or cylinder body 3 equipped with a gas inlet 1 and a gas outlet 2. The cylindrical body 3 is supported on a supporting means 4. The cylindrical body 3 is charged with a gas-adsorbing material 5. In the present specification, the gas-adsorbing apparatus may be used to include a combination of a main body, a gas inlet, a gas outlet, a supporting means and a gas-adsorbing material.

The gas inlet 1 and the gas outlet 2 are preferably connected respectively to gas-supplying pipe 6a and a gas-discharging pipe 6b via flexible or bendable tubes 7a and 7b, respectively. The provision of the flexible or bendable tubes between the gas inlet and gas outlet and the main gas-supplying pipes serves to enhance the sensitivity and accuracy of the weight measurement of the gas-adsorbing apparatus.

There is no specific limitation on the gas-adsorbing material placed in the gas-adsorbing apparatus. The gas-adsorbing material is so selected from the known adsorbing materials as to match with the gas to be adsorbed. Examples of the employable gas-adsorbing material include activated charcoal (i.e., activated crrbon), activated alumina, silica gel, titanium dioxide, bentonite, acid clay, diatomaceous earth, and calcium carbonate. The gas-adsorbing materials can be employed singly or in combination. Most preferred is activated charcoal. The gas-adsorbing material can be employed in the form of a surface-treated material according to the known process. Examples of the surface-treatment include applying a hydroxide or chloride of an alkaline earth metal to the activated charcoal. A known additive can be added to the gas-adsorbing material.

There is no specific limitation on the gas to which the present invention is applicable. Examples of the gas include chlorinated hydrocarbons, e.g., carbon tetrachloride and trichloroethylene, boron trichloride, halogen gases, ammonia gas, and silane gas. The gases can be used singly or in combination. The gas to be adsorbed can be any gas which is generated or exhausted in any process. For instance, a gas generated or exhausted in an LSI production using plasma CVD, industrial synthesis processes, or vapor-washing processes is treated to remove or recover all or a portion of the gas component(s). These gases can be diluted in other gas in advance of being supplied to the adsorption treatment.

In the system of FIG. 1, the gas is introduced into the gas-adsorbing apparatus through the gas inlet 1 and adsorbed by the gas-adsorbing material 5 enclosed in the main body 3. The gas is initially adsorbed by the column of adsorbing material 5 at the lower portion. Subsequently, the area actively adsorbing the gas (i.e., adsorption band) elevates gradually advancing toward the top of the column of the adsorbing material 5. Immediately after the adsorption band reaches the top of the column, the break-through starts to release the gas which was intended to be adsorbed.

The volume or amount of a gas adsorbable by a column of a gas-adsorbing material is almost the same, as far as the gas and the amount of the adsorbing material are the same. Accordingly, the break-through can be foreseen or detected by comparing a detected weight of the adsorbed gas with a predetermined weight of adsorbed gas at which the break-through starts. The predetermined weight at which the break-through starts can be beforehand determined by utilizing the same gas and the same gas-adsorbing apparatus. It can be designed that an alarm signal such as the sound of a buzzer or flicker of a lamp is given when the adsorption band reaches the predetermined level or the break-through just begins.

The predetermined amount for giving an alarm signal can be set to an optionally selected level, for instance, upon consideration of a period required for replacing the used gas-adsorbing apparatus with a fresh one. The predetermined amount is preferably set to be in a range of 80 to 99% (more preferably 90 to 95%) of the weight of adsorbed gas at which the break-through should start.

According to the present invention, the gas adsorbed by the adsorbing material is weighed by a weighing means. There is no specific limitation on the weighing means employable in the invention, and any of the known weighing means such as a spring balance can be used. Most preferred is a known load-cell type weighing means. The load-cell type weighing means is advantageously employed to sensitively detect increase of weight of a rather heavy article such as the adsorbing apparatus. Moreover, the load-cell type weighing means is advantageous in that the weight increase of the gas-adsorbing apparatus (which directly corresponds to increase of weight of the gas adsorbed by the adsorbing material) is directly detected as an electrical value so that the electrical value is relayed to an alarm means to emit an alarm signal. Furthermore, the use of a load-cell type weighing means is advantageous in that the zero-point adjustment which is required at the time of every replacement operation of the gas-adsorbing material can be easily done. Accordingly, the increase of weight of the adsorbed gas can be directly displayed on the scale of the load-cell type weighing means.

The load-cell type weighing means is already known. The load-cell type weighing means functions as a transducer in such a manner that the weight change is measured via change of an electrical output. Examples of the load-cell employable in the weighing means include a load cell of electroresistive strain gauge type, a load cell of differential transformer type, a load cell of magnetostriction type and a load cell of capacity transformer type. The load cell of electroresistive strain gauge type is preferred from the viewpoints of accuracy and reliability.

The load-cell type weighing means can be employed in various forms to measure the adsorbed gas. For instance, the adsorbing apparatus can be weighed on a scale means 8 equipped with a load cell therein, as illustrated in Fig. 1. Otherwise, the adsorbing apparatus can be directly supported on a plurality of load cells, or can be suspended via a load cell. The weight of the adsorbing apparatus is preferably measured by means of a load cell balance using a plurality of beams. Details of the preferred weighing means are seen in Japanese Utility Model Registration Application No. 54(1979)-119368. Also preferred is a weighing means of multi-load cell type using plural load cells in combination which directly support the adsorbing apparatus. Generally, the measurement of weight increase of the adsorbing apparatus (that is, the weight increase of the adsorbed gas) is continuously done.

The weighing means is generally associated with a detector 9 equipped with a warning means 10. The detector gives an electric signal to the warning means 10 when the weight of adsorbed gas reaches a predetermined or preset weight value which is preferably set to a value slightly less than the value at which the break-through just starts. The warning means 10 emits an alarm signal upon receiving an electric signal from the detector 9. In the case of using a load cell type weighing means, an electric signal is emitted when the weight of adsorbed gas reaches the preset value. In the case of using a spring balance, the weight increase can be read on the scale.

The weighing means can be associated with a detector equipped with a flow path-switching means. When a plurality of gas-adsorbing apparatuses are combined for replacement with one another through a branched pipe equipped with a flow path-switching valve, the valve may be operated by the switching means which is activated when the adsorbed gas reaches the preset value. The switching valve can be operated manually by an operator upon noting an alarm signal. In these arrangements using a combination of plural adsorbing apparatuses, the replacement of the adsorbing apparatus can be done with no loss of time.

The use of the weighing means for measurement of the adsorbed gas is further advantageous in that the weight of the employed gas is accurately determined. Accordingly, the amount of a remaining gas can be accurately known and failure orginating from shortage of etching gases hardly occurs.

The break-through of gaseous boron trichloride can be detected by detecting a color change of a specific detecting agent such as 1,1'-dianthrimide and a combination of carminic acid, hydrochloric acid and sulfuric acid. As seen in FIG. 1, the detecting agent 11 is arranged in a lower stream following the gas-adsorbing material. The detecting agent shows a color change upon contact with boron trichloride.

The above-mentioned two detecting agents are specifically sensitive to boron trichloride and show sharp color change upon contact with a small amount of boron trichloride.

1,1'-Dianthrimide is generally used in combination with concentrated sulfuric acid in which 1,1'-dianthrimide is employed in an amount of 0.05-2.0% by weight of the sulfuric acid. 1,1'-Dianthrimide shows green to pale green color in a conc. sulfuric acid solution. Upon contact with boron trichloride, this detecting agent sharply turns blue. The combination of 1,1'-dianthrimide and conc. sulfuric acid is generally supported on a carrier for the employment as the detecting agent. The carrier preferably is completely or almost colorless. For example, α-alumina, silica or silica alumina is employed as the carrier. The 1,1'-dianthrimide in combination with conc. sulfuric acid can sharply detect a very small amount such as 0.5 ppm of boron trichloride. It has been confirmed that all of other gases employable in combination with boron trichloride in industry for the dry-etching or metal surface-treating do not disturb such detection. However, 1,1'-dianthrimide can be adversely influenced in the presence of water. Accordingly, if the gas-adsorbing material contains more than a small amount of water, a water-adsorbing material such as synthetic zeolite having a molecular sieve function is preferably provided between the column of the adsorbing material and the detecting agent containing 1,1'-dianthrimide.

A combination of carminic acid, hydrochloric acid and sulfuric acid also can be employed as the detecting agent for boron trichloride. Generally, carminic acid is dissolved initially in concentrated sulfuric acid in an amount of 0.05-2.0%, preferably 0.1 to 1.0%, by weight based on the amount of sulfuric acid. Hydrochloric acid is generally employed in the form of known dilute hydrochloric acid (35%). The dilute hydrochloric acid can be combined with the sulfuric acid in an amount of 20-80% by weight based on the amount of the sulfuric acid. This combination advantageously contains copper sulfate in an amount of 0.01-1.0% (preferably 0.05-0.5%) by weight based on the amount of the sulfuric acid. The combination containing carminic acid is generally supported on a carrier in the same manner as in the 1,1'-dianthrimide. The combination containing carminic acid can sharply detect a very small amount such as 0.5 ppm of boron trichloride through sharp color change from very pale color or pale blue to pink. It has been confirmed that all of other gases used in combination with boron trichloride in industry for the dry-etching or metal surface-treating no not disturb such detection.

The above-mentioned detecting agents are very sensitive specifically to boron trichloride. Accordingly, these are advantageously employed for detecting break-through of boron trichloride in combination with the method of weighing the adsorbed gas.

Moreover, the detecting agent can be employed alone, that is, without using the adsorbed gas-weighing method, to detect the break-through of boron trichloride. It is further said that the very sensitive detecting agent is employable for foreseeing the break-through because the above-mentioned detecting agent detects a very small amount of released boron trichloride in advance of the occurrence of substantial break-through.

The present invention is further described by the following example.

A test run for foreseeing and detecting break-through was done using the gas-adsorbing apparatus as illustrated in FIG. 1. The weight of the gas-adsorbing apparatus charged with an adsorbing material was 100 kg. in which the weight of the adsorbing material was 18 kg. The measurement of the weight of the adsorbed gas was done through measurement of the weight of the gas-adsorbing apparatus using a weighing scale connected with a weighing means equipped with an electrosensitive strain gauge type load cell therein (available from Yamato Seiko Co., Ltd.). The connections with the gas inlet tube and the gas outlet tube to the main pipe systems are made through flexible tubes.

Adsorbing material: activated charcoal heated to 220° C. for 2 hours in a nitrogen gas Boron trichloride-detecting agent: 200 g. of conc. sulfuric acid containing 0.71 g. of 1,1'-dianthrimide which was supported on 467 g. of α-alumina carrier (mean particle size: 5 mm)

Gas to be adsorbed: boron trichloride($BCl_3$), chlorine gas, and nitrogen (diluent)

Flow rates: nitrogen, 0.5 l/min. boron trichloride, 0.26 l/min. chlorine gas, 0.10 l/min.

A gaseous stream of a mixture of boron trichloride and chlorine gas diluted with nitrogen was continuously introduced through the gas inlet into the gas-adsorbing apparatus. When the weight of the gas-adsorbing apparatus reached 113 kg., release of boron trichloride and chlorine gas from the top of the column of the adsorbing material was gas-chromatographically detected as well as detected by color change (change from none to blue) of the detecting agent (i.e., 1,1'-dianthrimide).

The whole of the used charcoal was replaced with fresh one, and a warning level of the weight increase was preset to 12 kg. The same gas-adsorbing operation was repeated using the adsorbing apparatus charged with the fresh activated charcoal, and the supply of gas stream was stopped when weight increase of the adsorbing apparatus reached 12 kg. At that time, neither boron trichloride nor chlorine gas was detected on the column of the charcoal. Thus, it was confirmed that no break-through occurred up to that time.

Similar test runs were performed using each of various gaseous mixtures, namely, $BCl_3$-$Cl_2$, $SiCl_4$-$CF_4$, and $SiCl_4$-$CCl_3F$, as a gas to be adsorbed. Almost the same results were obtained, and no break-through was detected when the supply of gas stream was terminated at a preset value which was determined in the same manner.

We claim:

1. In a method for foreseeing breakthrough of a gas in a gas-adsorbing apparatus utilizing a gas-adsorbing material, said gas-adsorbing apparatus being connected to a gas-supplying pipe and a gas-discharging pipe, the improvement in which the gas-adsorbing apparatus is connected to the gas-supplying pipe and gas-discharging pipe both via a flexible or bendable tube and is mounted on a load-cell type weighing means, and the break-through is foreseen by detecting the weight of the gas adsorbed by the gas-adsorbing material in the gas-adsorbing apparatus using the load cell type weighing means and by emitting an alarm signal when the weight of the adsorbed gas in said apparatus measured by said weighing means reaches a predetermined weight level, the predetermined weight level being set in the range of 80 to 99% of the weight of adsorbed gas at which the break-through would start.

2. The method as claimed in claim 1, in which the break-through is foreseen by comparing the detected weight of the adsorbed gas with a predetermined weight of adsorbed gas at which the break-through starts, the predetermined weight having been determined by utilizing the same gas and the same gas-adsorbing apparatus.

3. The method as claimed in claim 2, in which the break-through is foreseen by an alarm signal emitted when the weight of the adsorbed gas reaches a level of from 90 to 95% of the weight of adsorbed gas at which the break-through would start.

4. The method as claimed in claim 2, in which said gas is a gas containing boron trichloride.

5. The method as claimed in claim 1, in which said gas is a gas containing boron trichloride.

6. The method as claimed in claim 1, in which the gas to be detected contains boron trichloride and the break-through is further detected by observing a color change of a detecting agent selected from the group consisting of 1,1'-dianthrimide and a combination of carmic acid, hydrochloric acid and sulfuric acid, the detecting agent being arranged in a lower stream following the gas-adsorbing material and which shows a color change upon contact with boron trichloride.

* * * * *